Figure 2:
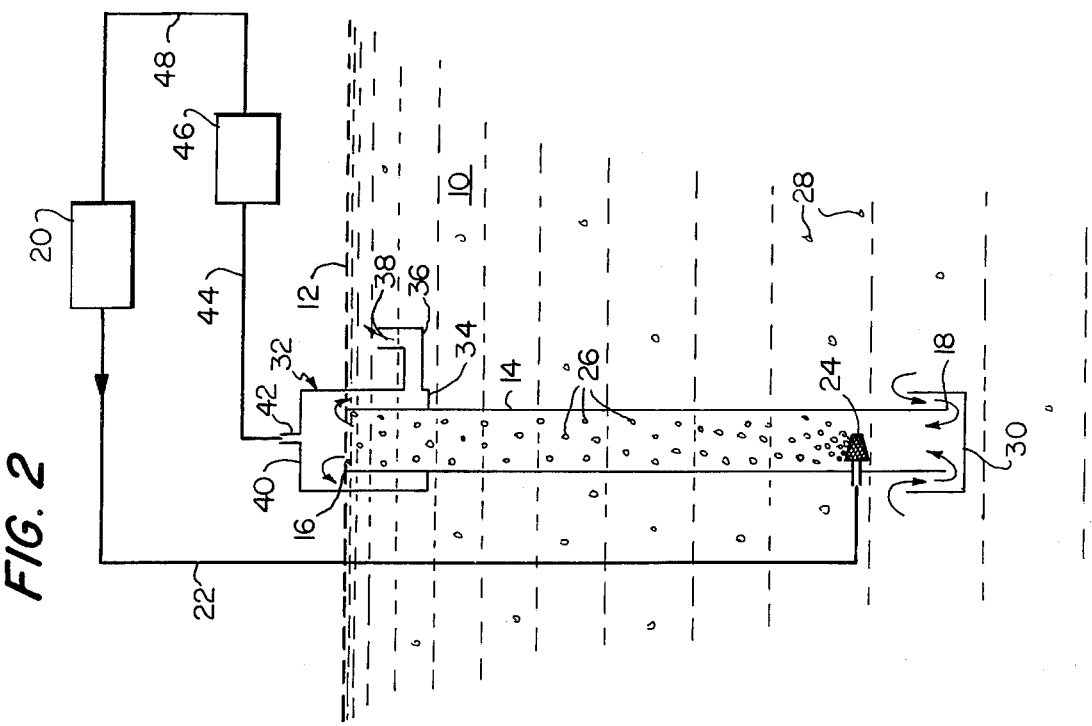

United States Patent [19]

Topol

[11] 3,942,792
[45] Mar. 9, 1976

[54] PROCESS AND APPARATUS FOR MEASURING DISSOLVED GAS

[75] Inventor: George J. Topol, Gaithersburg, Md.

[73] Assignee: Biospherics Incorporated, Rockville, Md.

[22] Filed: Apr. 18, 1974

[21] Appl. No.: 461,972

[52] U.S. Cl. .................................................. 273/19
[51] Int. Cl.² ........................................ G01N 7/00
[58] Field of Search ........................................ 73/19

[56] References Cited
UNITED STATES PATENTS

| | | | |
|---|---|---|---|
| 2,987,912 | 6/1961 | Jacobson | 73/19 |
| 3,068,684 | 12/1962 | Axt | 73/19 |
| 3,800,595 | 4/1974 | Vincent | 73/19 |

*Primary Examiner*—Richard E. Aegerter
*Assistant Examiner*—Steven L. Stephan
*Attorney, Agent, or Firm*—Roylance, Abrams, Berdo & Kaul

[57] ABSTRACT

There is disclosed a process and apparatus for measuring the amount of a dissolved gas in a liquid wherein the device used to measure the gas is not immersed in the liquid and wherein there is no requirement that a sample of the liquid be removed from the main body of the liquid to be tested. A vertical zone is provided in the body of liquid which is to be measured for the amount of gas contained in the liquid, such as in the aeration tank in a sewage treatment system. The zone is at least partially open at the lower end so that it is in communication with the body of liquid and is closed to contact with the body of liquid on the sides. A gas is passed into the lower portion of the zone and a gas-lift effect is created in the zone. Gas is recovered at the upper portion of the zone and is returned to the lower portion of the zone, thereby creating a closed recirculating gas system — i.e., the system is closed to the atmosphere and to the liquid outside of the zone. The gas-lift effect causes liquid to continuously overflow the top of the zone from which it is returned to the body of liquid outside of the zone and additional liquid enters the lower portion of the zone from the body of liquid outside of the zone. Recirculation of the gas is continued to establish an equilibrium between the recirculating gas and the liquid in the zone as to the dissolved gas to be measured. When this equilibrium has been reached, the amount of dissolved gas which has been extracted into the recirculating gas is measured by a gas measuring means which is not in contact with the liquid containing the dissolved gas.

13 Claims, 2 Drawing Figures

PROCESS AND APPARATUS FOR MEASURING DISSOLVED GAS

This invention relates to a method and apparatus for measuring the amount of a dissolved gas in a liquid, and, more particularly, for measuring the amount of dissolved oxygen in water.

The level of dissolved oxygen in water is extremely important in sewage treatment facilities as well as in natural bodies of water, such as rivers and streams. For example, in an activated sludge sewage treatment process, the operational cost for performing the process is affected significantly by the amount of energy consumed by the aeration equipment. In order for the microorganisms present in an activated sludge sewage treatment process to be most effective, the oxygen level should be maintained at or above about 2 ppm of sewage. To maintain the dissolved oxygen level at the desired level, it is common practice to provide large blowers or other devices which aerate the sewage in an aeration tank. Since the operation of more blowers than are necessary to furnish the required amount of dissolved oxygen is a costly waste of energy, an adequate blower control system is desirable — i.e., a means for monitoring the dissolved oxygen content in the sewage so that the rate of aeration may be increased or decreased as required.

There are several types of devices for measuring the dissolved oxygen content of the liquid on the markets. One type in common use involves the utilization of a membrane electrode system. The basic structure of such a system includes a two solid electrode cell, a thin layer of supporting electrolyte in direct contact with the electrodes and an oxygen permeable membrane which separates the electrodes and the electrolyte solution from the test solution. This device is conventionally immersed in the liquid which is to be measured for dissolved oxygen, such as the sewage in an aeration basin. In order to continuously monitor the dissolved oxygen content of the sewage, it is necessary to leave the device immersed in the sewage. A disadvantage of this technique is that slime quickly forms on the apparatus, rendering the membrane inoperative.

There are devices known in the prior art which provide for the measurement of a dissolved gas in a liquid wherein the dissolved gas measuring device is not immersed in the liquid. Thus, U.S. Pat. No. 2,987,912 to Jacobson discloses a closed system for the measurement of a gas, such as dissolved oxygen in sewage, in which a sample of a liquid to be analyzed for dissolved gas is flushed by introducing bubbles of a neutral gas near the bottom of a closed chamber containing the liquid. The neutral gas together with the released dissolved gas from the sample vessel is recirculated until the measuring means gives a constant response — i.e., until an equilibrium is established between the neutral gas and the liquid in the closed chamber as to the dissolved gas. However, according to the teachings of this patent, the entire system is located outside of the body of liquid which is to be analyzed for dissolved gas, and it is necessary to withdraw liquid from the body of liquid to be measured and pass it to a separate closed container. When such a system would be used to measure the dissolved oxygen content of sewage, it would be necessary to provide a separate pump and pipe to transport the sewage from the aeration basin to the measuring tank. This not only requires the use of additional equipment but also requires that care be taken under some circumstances, such as cold weather, so that the line between the aeration basin and the measuring tank would not freeze.

It is an object of this invention to provide a method and apparatus for measuring the amount of a dissolved gas in a liquid wherein the device used to measure the dissolved gas is not immersed in the liquid.

It is another object of this invention to provide such a method and apparatus which eliminates the requirement that a sample of the liquid be removed from the main body of liquid to be tested.

These and other objects are attained by the practice of this invention which, briefly, comprises providing a vertical zone in the body of liquid which is to be measured for the amount of gas contained in the liquid, such as in the aeration tank in a sewage treatment system. The zone is at least partially open at the lower end so that it is in communication with the body of liquid and is closed to contact with the body of liquid on the sides. A gas is passed into the lower portion of the zone and a gas-lift effect is created in the zone. Gas is recovered at the upper portion of the zone and is returned to the lower portion of the zone, thereby creating a closed recirculating gas system — i.e., the system is closed to the atmosphere and to the liquid outside of the zone. The gas-lift effect causes liquid to continuously overflow the top of the zone from which it is returned to the body of liquid outside of the zone and additional liquid enters the lower portion of the zone from the body of liquid outside of the zone. Recirculation of the gas is continued to establish an equilibrium between the recirculating gas and the liquid in the zone as to the dissolved gas to be measured. When this equilibrium has been reached, the amount of dissolved gas which has been extracted into the recirculating gas is measured by a gas measuring means which is not in contact with the liquid containing the dissolved gas.

Figure 1:
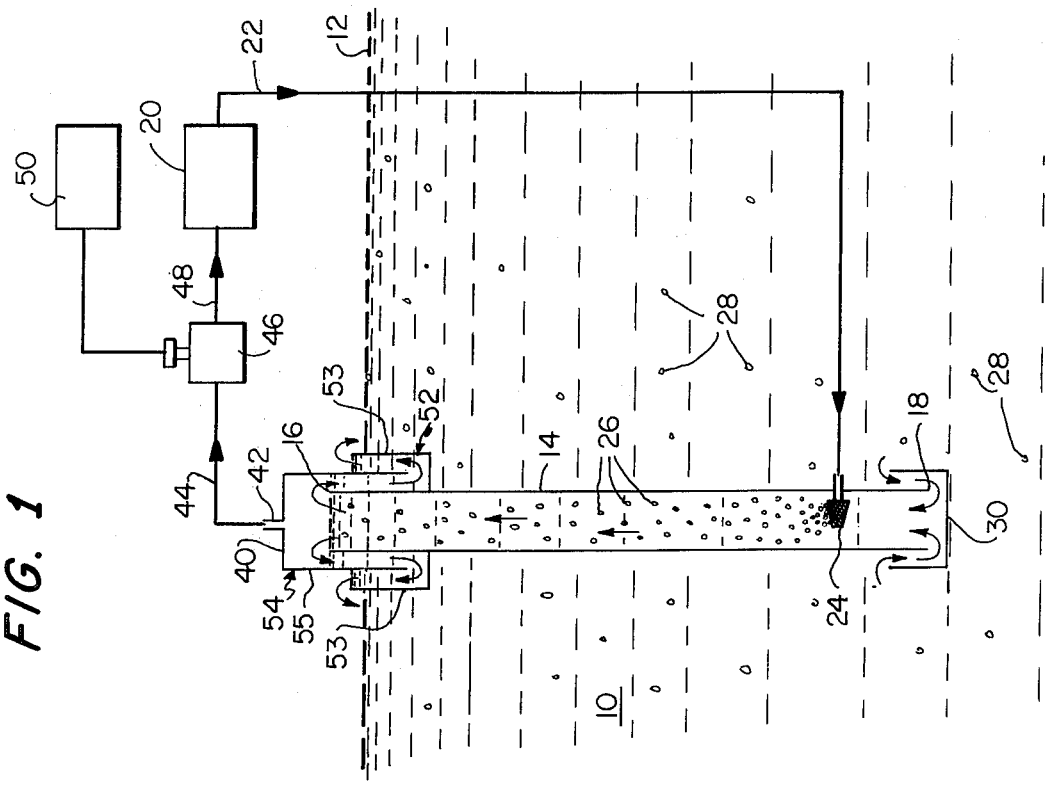

This invention will be described in further detail in connection with the accompanying drawings wherein FIGS. 1 and 2 are schematic diagrams illustrating two different embodiments of an apparatus which may be used in the practice of this invention.

Referring to FIG. 1, there is shown a section of an aeration tank 10 such as is used in a conventional activated sludge sewage treatment process. The level of sewage or waste water is indicated at 12. A vertical zone is provided within the body of sewage by means of the cylindrical tube 14 which is open at the top end 16 and the bottom end 18. An air pump 20 pumps air through a conduit 22 into a gas diffuser or bubbling device 24 located inside the cylindrical tube 14 and near the bottom thereof. There is thereby created a large number of upwardly moving bubbles 26 within the cylindrical tube 14.

Outside of the cylindrical tube 14, there are a number of upwardly moving air bubbles 28 which are produced by the aeration apparatus used to aerate the sewage in the aeration tank 10. It is preferred to keep these bubbles out of the cylindrical tube 14 since they are not in dissolved oxygen equilibrium with the sewage. Accordingly, an upwardly opening cylindrical cap 30 is placed over the bottom end 18 of the cylindrical tube 14 and is spaced apart from the bottom end 18 so that sewage from the main body of waste water contained in the aeration tank 10 is free to flow into the bottom end 18 and the upwardly moving air bubbles 28 are excluded therefrom.

The top end 16 of the cylindrical tube 14 in FIG. 2 is covered by a cylindrical cap 32 which is closed at its lower end 34 by an annular surface which surrounds and engages the outer surface of the cylindrical tube 14. An exit tube 36 is connected to the lower portion of the cap 32. The exit tube 36 has an opening 38 in the end thereof from which fluid contained in the cylindrical tube 14 and the cap 32 can emerge.

The cap 32 has an upper surface 40 which is closed except for a vent 42 which connects with a conduit 44. The top 40 of the cap 32 extends above the level of the sewage 12 so that a space exists in the upper portion of the cap 32 above the water level 12. The vent 42 and the conduit 44 conduct gas from the cap 32 to an oxygen sensor 46. The gas which has passed through the oxygen sensor 46 is returned by a conduit 48 to the air pump 20.

The conduits 22, 44 and 48 together with the air pump 20, the cap 32, the oxygen sensor 46 and the bubble path from the diffuser 24 to the cap 32 constitute a completely closed system for the gas which is caused to bubble through the sewage which is within the cylindrical tube 14. Thus, the same gas is recirculated through this closed system so that an equilibrium is reached between the recirculating gas and the waste water contained in the cylindrical tube 14 as to dissolved oxygen. The composition of the initial gas which is first pumped into the diffuser 24 is of no consequence since, once the recirculating gas reaches equilibrium with the liquid, the composition of this recirculating gas will be the same regardless of what gas was first pumped into the diffuser 14. Thus, if the dissolved oxygen content of the sewage is about 2 ppm and air is initially introduced into the diffuser 14, the oxygen content of the recirculating gas as measured by the oxygen sensor 46 will fall until it reaches equilibrium with the waste water. On the other hand, if a non-oxygen containing gas such as nitrogen is initially introduced into the diffuser 24, the oxygen content of the recirculating gas will increase until it reaches eqilibrium with the waste water.

Any type of gas measuring or detecting means may be used in the practice of this invention such as a polarographic membrane type probe as described in a brochure by Weston and Stack, Inc., entitled "Fundamentals of Molecular Oxygen Measurement With Polarographic Membrane-Type Probes"; a membrane electrode system as described in *Water Quality Instrumentation*, Vol. I., pages 278 to 282; or an oxygen sensor as described in a paper entitled "The Application of Polarographic Dissolved Oxygen Sensors to Municipal and Industrial Waste Water Treatement," presented at the 15th National Symposium of the Analysis Instrumentation Division of the Instrument Society of America on May 5 to 7, 1969, and which was reprinted in *Instrumental Analysis for Water Pollution Control*, published by Ann Arbor Science Publishers, Inc., pages 99 to 113. The disclosures of each of these literature references are incorporated herein by reference.

The oxygen sensor 46 may be attached to a meter or recorder 50, shown in FIG. 1, which will visually show or automatically record the oxygen content of the recirculating gas which, being in equilibrium with the waste water as to dissolved oxygen, will be directly proportional to the dissolved oxygen content in the waste water in the cylindrical tube 14. Moreover, the oxygen sensor 46 may be connected to an actuating means which will start up a blower and increase the rate of aeration when the dissolved oxygen content falls below 1 or 2 ppm and/or to shut off an aerator if the dissolved oxygen content goes above the optimum level. The amount of gas dissolved in the body of liquid may be continuously monitored or intermittently measured.

The recirculating gas which is introduced through the diffuser 24 serves not only as a means to measure the oxygen content of a liquid contained in the cylindrical tube 14 but also provides a gas-lift effect within the tube 14. Thus, the mixture of gas and water in the tube 14 is lighter than the waste water surrounding the tube 14 and, as a result, the mixture of gas and water is forced upward by the pressure of the heavier waste water exerted at the lower portion of the tube 14. The waste water in the cylindrical tube 14 overflows the top end 16 into the cap 32 and is returned to the main body of sewage through the exit 36 as indicated by the arrows. To replace the liquid which is forced out of the top of the cylindrical tube 14 by this gas-lift effect, liquid from the surrounding body of waste water enters the bottom end 18 of the cylindrical tube 14 as indicated by the arrows. Thus, there is a continuous circulation between the waste water contained in the cylindrical tube 20 and the surrounding waste water contained in the aeration tank 10. The closed gas system previously described permits the recirculating gas to reach an equilibrium level not only with the liquid within the cylindrical tube 14 but also with the entire body of surrounding waste water as represented by the sample contained in the cylindrical tube 14. In other words, the waste water in the cylindrical tube 14 contains essentially the same amount of dissolved oxygen as does the waste water surrounding this tube.

Another means which may be used to enclose the top end 16 is shown in FIG. 1. A housing 52 having a U-shaped cross section surrounds and engages the outer surface of the cylindrical tube 14. The legs 53 of the housing 52 extend slightly above the level of the sewage 12 in the aeration tank 10. A downwardly opening cylindrical cap 54 is placed over the top end 16. The top 40 of the cap 54 and the legs 55 of the cap 54 are in spaced relationship from the top and sides of the cylindrical tube 14. The legs 55 of the cap 54 are situated between the legs 53 of the housing 52 and the sides of the cylindrical tube 14.

In order for the gas-lift effect to be operative, the end of the cylindrical tube 14 may be located below the level of sewage 12 or at the same level or it may be somewhat above this level. However, the top end 16 of the cylinder should not be so far above the level of the sewage in the aeration tank that the gas-lift effect will not cause the waste water contained in the cylinder 14 to overflow the top end 16.

The following example illustrates the practice of this invention:

EXAMPLE

An apparatus as shown in FIG. 1 is placed in the aeration tank of an activated sludge sewage treatment system. The apparatus is situated near the end of the aeration tank at which the sewage is withdrawn and passed to a secondary clarifier. The cylindrical tube 14 is about 3 feet high and has a capacity of about 5 liters. Air is pumped into the diffuser at a rate of about 1 liter per minute. The recirculating gas in the closed system has total volume of about 1 liter and reaches equilibrium with the waste water in about 10 minutes — i.e., after the total volume of air has been recirculated about 10 times. After the recirculating gas has equilibrated with the liquid in the aeration basin, the dissolved oxygen content of the sewage is determined to be about 2 ppm. The dissolved oxygen content of the sewage is continuously monitored on this apparatus and is maintained at about 2 ppm plus or minus 1 ppm.

I claim:

1. A method for measuring the amount of a gas dissolved in a body of liquid which comprises:
   a. providing a vertical zone in said body of liquid, said zone being at least partially open at the lower end thereof so that it is in communication with said body of liquid and being closed to contact with said body of liquid on the sides,
   b. passing a gas into a lower portion of said zone and creating a gas-lift effect in said zone,
   c. recovering gas at the upper portion of said zone and returning said gas to said lower portion of said zone, thereby creating a recirculating gas system which is closed to the atmosphere and to the liquid outside of said zone,
   d. withdrawing liquid from the top of said zone returning it to said body of liquid outside of said zone and introducing additional liquid into the lower portion of said zone from said body of liquid by means of said gas-lift effect,
   e. continuing the recirculation of the gas to establish an equilibrium between the recirculating gas and the liquid in said zone as to the dissolved gas to be measured, and
   f. measuring the amount of gas to be measured contained in the recirculating gas by a gas measuring means which is not in contact with said liquid.

2. A method as defined in claim 1 wherein the dissolved gas is oxygen.

3. A method as defined in claim 2 wherein said oxygen is dissolved in sewage or other waste water.

4. A method as defined in claim 1 wherein said zone is partially covered at the lower portion thereof to exclude bubbles of gas contained in said body of liquid from entering said zone.

5. A method as defined in claim 1 wherein the amount of gas dissolved in said body of liquid is continuously monitored.

6. A method as defined in claim 1 wherein the amount of gas dissolved in said body of liquid is intermittently monitored.

7. A system for measuring the amount of gas dissolved in a body of liquid which comprises a hollow, vertical column which is at least partially immersed in said body of liquid and at least partially open at the bottom end thereof so that it is in communication with said body of liquid and a means at the top end thereof for closing the end of said column to contact with the surrounding environment, means for creating a recirculating gas system which is closed to the atmosphere and to said body of liquid which includes means for passing a gas into the lower portion of said column and means for withdrawing gas from the top of said column, thus creating a gas-lift effect within said column that circulates liquid from said body through said column and means for measuring the amount of a particular gas contained in the recirculating gas.

8. An apparatus as defined in claim 7 wherein said means for introducing a gas into the lower portion of said column includes a gas diffuser situated in the lower portion of said column.

9. An apparatus as defined in claim 7 wherein the lower portion of said column is provided with an upwardly opening cylindrical cap which is spaced apart from the bottom end thereof so that liquid from said body of liquid may flow into the bottom end of said column but gas bubbles contained in said body of liquid are excluded from entering said column.

10. An apparatus as defined in claim 7 wherein said means for withdrawing gas from the top of said column includes a cap which surrounds the upper portion of said column.

11. An apparatus as defined in claim 10 wherein said cap contains a vent in the top thereof which is in gas tight communication with the means for introducing gas into the bottom portion of said column.

12. An apparatus as defined in claim 11 wherein said cap is closed at its lower end by a surface which surrounds and engages the outer surface of the column, an exit tube being connected to the lower portion of the cap, said exit tube having an opening therein, the top and sides of said cap being spaced from the top and sides of said column.

13. An apparatus as defined in claim 11 wherein the means for withdrawing gas from the upper portion of said column includes a housing having a U-shaped cross section which surrounds and engages the outer surface of the column, and a downwardly opening cap which is located over the top end of said column, the top and sides of said cap being spaced from the top and sides of said column and the legs of said cap being situated between the legs of said housing and the legs of said column.

* * * * *